(12) United States Patent
Lindacher

(10) Patent No.: US 7,237,894 B2
(45) Date of Patent: Jul. 3, 2007

(54) MULTIFOCAL OPHTHALMIC LENS

(75) Inventor: Joseph Michael Lindacher, Lawrenceville, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/406,108

(22) Filed: Apr. 18, 2006

(65) Prior Publication Data

US 2006/0192919 A1    Aug. 31, 2006

Related U.S. Application Data

(62) Division of application No. 10/822,564, filed on Apr. 12, 2004, now Pat. No. 7,063,422.

(60) Provisional application No. 60/463,210, filed on Apr. 16, 2003.

(51) Int. Cl.
*G02C 7/02* (2006.01)
*A61B 18/18* (2006.01)

(52) U.S. Cl. .............................. 351/177; 606/4; 606/5; 351/161

(58) Field of Classification Search ................ 351/177; 606/4
See application file for complete search history.

(56) References Cited

U.S. PATENT DOCUMENTS

| | | | | |
|---|---|---|---|---|
| 5,557,348 | A | * | 9/1996 | Umeda et al. ............... 351/169 |
| 5,683,456 | A | * | 11/1997 | Blake .......................... 623/6.23 |
| 6,059,775 | A | * | 5/2000 | Nielsen .......................... 606/5 |
| 6,595,639 | B1 | * | 7/2003 | Ho et al. ..................... 351/177 |
| 6,746,119 | B2 | * | 6/2004 | Ezekiel ....................... 351/161 |

* cited by examiner

*Primary Examiner*—Jordan Schwartz
*Assistant Examiner*—Jessica Stultz
(74) *Attorney, Agent, or Firm*—Jian Zhou; Sheng-Hsin Hu

(57) ABSTRACT

This invention is generally related to vision corrections by means of multifocal ophthalmic lenses or by means of corneal refractive surgery. In particular, the present invention provides a multifocal contact lens, a multifocal intraocular lens, a method for making a multifocal ophthalmic lens (contact lens and intraocular lens), and a method of correcting presbyopia by reshaping the cornea of an eye.

12 Claims, 4 Drawing Sheets

MULTIFOCAL OPHTHALMIC LENS

This application is a division of U.S. patent application Ser. No. 10/822,564 filed Apr. 12, 2004 now U.S. Pat. No. 7,063,422, which claims the benefit under 35 USC § 119 (e) of U.S. provisional application No. 60/463,210, filed Apr. 16, 2003, incorporated by reference in its entirety.

This invention is generally related to vision corrections by means of multifocal ophthalmic lenses or by means of corneal refractive surgery. In particular, the present invention provides a multifocal contact lens, a multifocal intraocular lens, a method for making a multifocal ophthalmic lens (contact lens and intraocular lens), and a method of correcting presbyopia by reshaping the cornea of an eye.

BACKGROUND

It is believed that presbyopia occurs as a person ages when the lens of eye loses its elasticity, eventually resulting in the eye losing the ability to focus at near distances (when distance vision is corrected), such as the normal reading distance, and in some cases at intermediate distances. Presbyopic persons (presbyopes) complain of difficulty performing close tasks. To compensate for presbyopia, ophthalmic lenses are required to be more positively powered or less negatively powered than the distance correction. Some presbyopic persons have both near vision and distance vision defects, requiring simultaneous or alternating vision lenses, instead of single vision lenses, to properly correct their vision.

A typical single vision contact lens has a real or virtual focus, which is the point on which parallel rays of light focus when the lens is placed perpendicular to the parallel rays, and an optical axis, which is an imaginary line drawn from the focus to the center of the lens. A posterior surface fits against the cornea and an opposite anterior surface has a vision surface that focuses light to correct the eye's vision. In the case of a typical spherical optical zone surface lens, the vision surface has a single radius of curvature that is the distance from any point on the vision surface to a point on the optical axis referred to as the center of curvature.

Simultaneous vision refers to the class of bifocal or multifocal contact lenses in which optical power for distance vision and near vision are positioned simultaneously within the pupil area of a user's eye. The conventional clinical understanding for simultaneous vision is that a bifocal lens projects both distance and near images simultaneously onto the retina. Depending on the viewing distance of the object of regard, one of the images is in focus, and the other image is out of focus. It is believed that the brain is able to discriminate between the irrelevant out-of-focus image and to process only the relevant in-focus image. Therefore, whether an object is at distance or near locations, the lens is still able to provide levels of vision that may be acceptable to many patients.

Simultaneous vision contact lenses are generally composed of, within the pupil area of the eye, two or more concentric annular zones which alternately provide the distance and near power, or a multifocal zone having an aspheric surface which provides a continuous gradient of optical power over a selected range of powers. The visual performance of the simultaneous vision lens design is limited by its dependence on pupil size. Moreover, with all simultaneous vision lenses a partially degraded image of an object is projected onto the retina. The consequence of this image degradation is a reduction in visual activity and/or contrast sensitivity (less signal, more noise), and the quality of the degraded image may or may not be acceptable to the patient. The clinical effects of this degradation may be measured objectively in terms of reduced visual acuity and contrast sensitivity. The subjective effects of the degradation are perceived by the patient in various ways which are collectively referred to as subjective blur. Therefore, when wearing a simultaneous vision lens, the patient may not be selecting between separate distance and near images. Rather, in the presence of subjective blur the patient may be attempting to function with the reduced level of spatial information content that is provided by a degraded image.

Alternating vision refers to the class of segmented (or translating) bifocal contact lenses in which the lens is divided into two optical zones. Typically the superior (or upper) zone is for distance vision correction, whereas the lower zone is for near vision correction. The distance portion (upper zone) subtends the pupil of the eye in primary gaze, while in downward gaze, the add power or near portion (lower zone) of the lens subtends the pupil. Effective use of an alternating vision lens requires vertical translation of the optical zones across the pupil when the eye changes from primary gaze to a downward gaze. In such a situation, the lens must move such that the pupil is predominately subtended by the distance zone for primary gaze and predominately subtended by the near zone for down-gaze. The visual performance of the alternating vision lens design is not significantly limited by its dependence on pupil size.

While there are many designs for hard bifocal translating contact lenses, controlled rotational stability and translation are difficult to achieve in soft contact lenses designed to translate across the surface of the eye when the visual direction of the eye changes from primary gaze (distance vision) to down gaze (near vision). There are several lens designs reported for soft bifocal translating lenses (see, for example, U.S. Pat. Nos. 4,618,277, 5,071,244, 5,371,976, 6,109,749). However, there are some disadvantages associated with those designs (for hard and soft translating bifocal contact lenses) in the prior art. First, bifocal translating contact lenses in the prior art are not comfortable to be worn. Second, the images from different optical zones in bifocal translating contact lenses in the prior art have lateral separation, causing ghost images to the wearer. Specifically, in a bifocal, segmented optical zone contact lens, the images, on the retina, from both an upper and lower optical zones can not be laterally coincident to minimize or eliminate ghost images. Therefore, bifocal translating contact lenses in the prior art can not provide clear or optimized vision to wearers.

Additionally, with the increasing use of computers, more and more people utilize a computer at work and at home. It is desirable that a translating contact lens could have one or more intermediate vision zones in addition to the near and distant vision surfaces. For example, it is desirable that the optical zone of a translating contact lens could have a continuous power profile or discrete optical sub-zones blend together or combinations thereof. Such a translating contact lens may have to have an ability to control the rotational stability and translation magnitude on the eye in a manner that the pupil can be subtended by one of near vision surface, intermediate vision surfaces, and distant vision surface.

Therefore, there is a need for a new type of multi-focal contact lenses, which are capable of providing distance, intermediate, and near vision corrections and have a visual performance that may not be limited by their dependence on pupil size.

SUMMARY OF THE INVENTION

The invention, in one aspect, provides a contact lens capable of correcting presbyopia by providing distance, intermediate and near vision corrections. The contact lens has an anterior surface and an opposite posterior surface. One of the anterior and posterior surface, preferably the anterior surface, comprises a vertical meridian, a horizontal meridian, and a central optical zone. The central optical zone includes a distance vision zone and a rotationally-asymmetrical progressive zone adjacent to the distance vision zone. The distance vision zone is located in the upper portion of the central optical zone and provides a distance power for distance vision correction. The rotationally-asymmetrical progressive zone is located in the lower portion of the central optical zone and provides a variable intermediate vision correction and near vision correction. Preferably, the rotationally-asymmetrical progressive zone has an upper boundary, a lower boundary, a radial center, an upper vertically radiating semi-meridian and a lower vertically radiating semi-meridian. The rotationally-asymmetrical progressive zone further has a surface that provides a power profile that increases, along the upper vertically radiating semi-meridian, from the distance power at the upper boundary to a near power at the radial center and remains substantially constant from the radial center to a point near the lower boundary along the lower vertically radiating semi-meridian.

The invention, in another aspect, provides an intraocular lens capable of correcting presbyopia by providing distance, intermediate and near vision corrections. The intraocular lens can be phakic or aphakic. The intraocular lens comprises a central optical zone, the central optical zone having a first surface and an opposite second surface. At least one of the first and second surfaces includes a vertical meridian, a horizontal meridian, a distance vision zone and a rotationally-asymmetrical progressive zone adjacent to the distance vision zone. The distance vision zone is located in the upper portion of the central optical zone and provides a distance power for distance vision correction. The rotationally-asymmetrical progressive zone is located in the lower portion of the central optical zone and provides a variable intermediate vision correction and near vision correction. Preferably, the rotationally-asymmetrical progressive zone has an upper boundary, a lower boundary, a radial center located in the vertical meridian and below the center of the optical zone. The rotationally-asymmetrical progressive zone further has a surface that provides a power profile that increases, along the vertical meridian, from the distance power at the upper boundary to a near power at the radial center and then remains substantially constant from the radial center to a point near the lower boundary along the vertical meridian.

The invention, in still another aspect, provides a method for producing a contact lens capable of correcting presbyopia by providing distance, intermediate and near vision corrections. The method comprises the steps of designing the anterior surface and the posterior surface of the contact lens, wherein one of the anterior and posterior surface, preferably the anterior surface, includes a vertical meridian, a horizontal meridian, a central optical zone having a distance vision zone and a rotationally-asymmetrical progressive zone adjacent to the distance vision zone. The distance vision zone is located in the upper portion of the central optical zone and provides a distance power for distance vision correction. The rotationally-asymmetrical progressive zone is located in the lower portion of the central optical zone and provides a variable intermediate vision correction and near vision correction. Preferably, the rotationally-asymmetrical progressive zone has an upper boundary, a lower boundary, a radial center, an upper vertically radiating semi-meridian and a lower vertically radiating semi-meridian. The rotationally-asymmetrical progressive zone further has a surface that provides a power profile that increases, along the upper vertically radiating semi-meridian, from the distance power at the upper boundary to a near power at the radial center and remains substantially constant from the radial center to a point near the lower boundary along the lower vertically radiating semi-meridian.

The invention, in a further aspect, provides a method for producing an intraocular lens capable of correcting presbyopia by providing distance, intermediate and near vision corrections. The method comprises the steps of designing the intraocular lens which comprises a central optical zone, the central optical zone having a first surface and an opposite second surface. At least one of the first and second surfaces includes a vertical meridian, a horizontal meridian, a distance vision zone and a rotationally-asymmetrical progressive zone adjacent to the distance vision zone. The distance vision zone is located in the upper portion of the central optical zone and provides a distance power for distance vision correction. The rotationally-asymmetrical progressive zone is located in the lower portion of the central optical zone and provides a variable intermediate vision correction and near vision correction. Preferably, the rotationally-asymmetrical progressive zone has an upper boundary, a lower boundary, a radial center located in the vertical meridian and below the center of the optical zone. The rotationally-asymmetrical progressive zone further has a surface that provides a power profile that increases, along the vertical meridian, from the distance power at the upper boundary to a near power at the radial center, and then remains substantially constant from the radial center to a point near the lower boundary along the vertical meridian.

The invention, in a further aspect, provides a method for correcting presbyopia, comprises the step of reshaping the central vision area of the cornea of an eye to produce an optical zone, which includes a vertical meridian, a horizontal meridian, a distance vision zone and a rotationally-asymmetrical progressive zone adjacent to the distance vision zone. The distance vision zone is located in the upper portion of the central vision area and provides a distance power for distance vision correction. The rotationally-asymmetrical progressive zone is located in the lower portion of the central vision area and provides a variable intermediate vision correction and near vision correction. The rotationally-asymmetrical progressive zone has an upper boundary, a lower boundary, a radial center located in the vertical meridian of the central vision area and below the center of the central vision area. The rotationally-asymmetrical progressive zone further has a surface that provides a power profile that increases, along the vertical meridian, from the distance power at the upper boundary to a near power at the radial center, and then remains substantially constant from the radial center to a point near the lower boundary along the vertical meridian.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAIL DESCRIPTION OF THE INVENTION

Figure 1A:
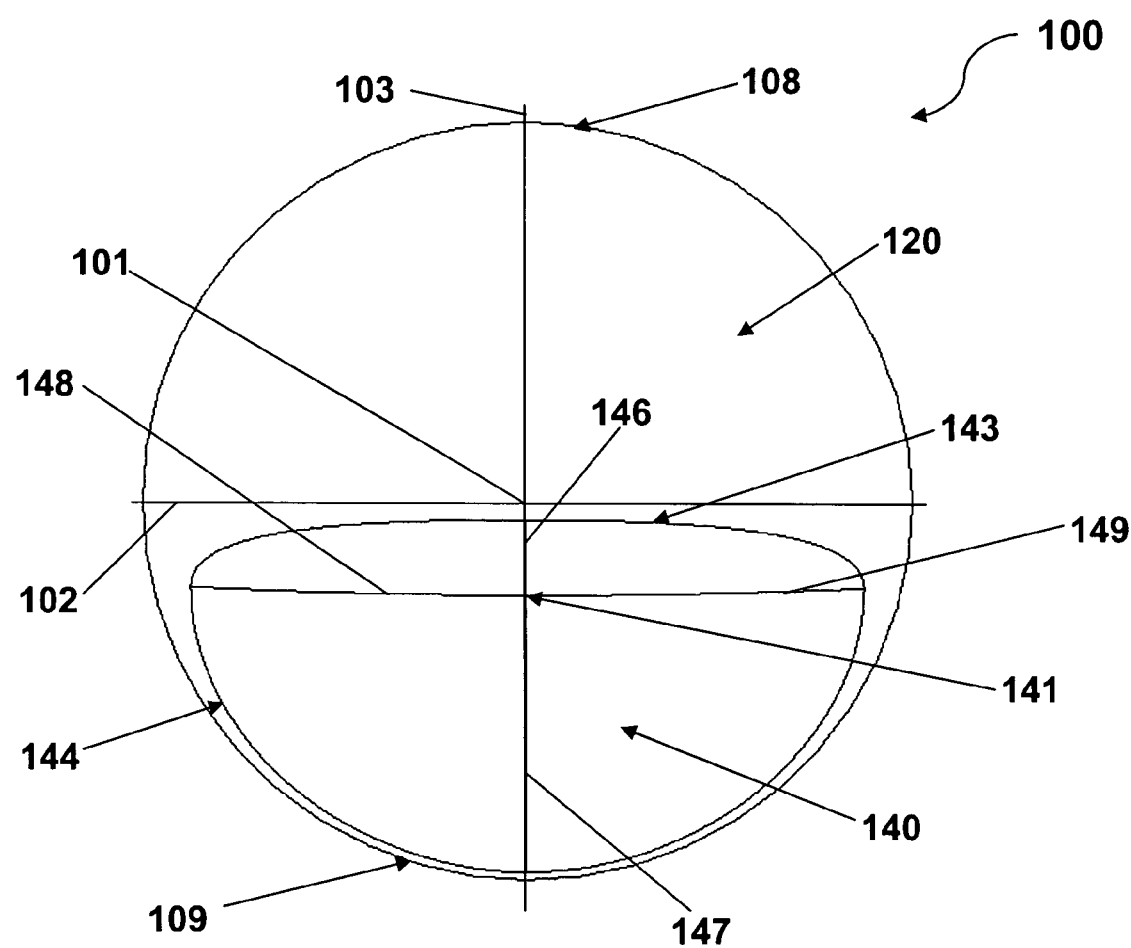
FIGS. 1A and 1B illustrate schematically the central optical zone of the anterior surface of a contact lens according to a preferred embodiment of the invention.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Unless defined otherwise, all technical and scientific terms used herein have the same meanings as commonly understood by one of ordinary skilled in the art to which this invention belongs. Generally, the nomenclature used herein and the laboratory procedures are well known and commonly employed in the art. Conventional methods are used for these procedures, such as those provided in the art and various general references.

The present invention is generally related to correcting presbyopia by means of multifocal ophthalmic lenses or by means of corneal refractive surgery.

In one aspect, the invention provides a contact lens capable of correcting presbyopia by providing distance, intermediate and near vision corrections. The contact lens has an anterior surface and an opposite posterior surface. One of the anterior and posterior surfaces, preferably the anterior surface, comprises a vertical meridian, a horizontal meridian, and a central optical zone. The central optical zone includes a distance vision zone and a rotationally-asymmetrical progressive zone adjacent to the distance vision zone. The distance vision zone is located in the upper portion of the central optical zone and provides a distance power for distance vision correction. The rotationally-asymmetrical progressive zone is located in the lower portion of the central optical zone and provides a variable intermediate vision correction and near vision correction.

In a preferred embodiment, the rotationally-asymmetrical progressive zone has an upper boundary, a lower boundary, a radial center, an upper vertically radiating semi-meridian and a lower vertically radiating semi-meridian. The rotationally-asymmetrical progressive zone further has a surface that provides a power profile that increases, along the upper vertically radiating semi-meridian, from the distance power at the upper boundary to a near power at the radial center and remains substantially constant from the radial center to a point near the lower boundary along the lower vertically radiating semi-meridian.

A "vertical meridian", in reference to an ophthalmic lens, refers to an imaginary line running vertically from the top, through the center, to the bottom on one of the anterior surface and posterior surface of a contact lens or on one of the two opposite surfaces of the central optical zone of an intraocular lens, when said lens is maintained at a predetermined orientation on or in an eye. A "horizontal meridian", in reference to an ophthalmic lens, refers to an imaginary line running horizontally from the left side, through the center, to the right side on one of the anterior surface and posterior surface of a contact lens or on one of the two opposite surfaces of the central optical zone of an intraocular lens, when said lens is maintained at a predetermined orientation on or in an eye. The horizontal and vertical meridians are perpendicular to each other.

A "top boundary", in reference to the central optical zone of a contact lens or an intraocular lens, refers to a portion of the peripheral boundary of the central optical zone, which is above the horizontal meridian and around the intersection of a line with the peripheral boundary, wherein the line is parallel to the vertical meridian and passes through the center of the central optical zone.

A "bottom boundary", in reference to the central optical zone of a contact lens or an intraocular lens, refers to a portion of the peripheral boundary of the central optical zone, which is below the horizontal meridian and around the intersection of a line with the peripheral boundary, wherein the line is parallel to the vertical meridian and passes through the center of the central optical zone.

A "variable intermediate vision correction", in reference to an optical zone of a lens (contact lens or intraocular lens), refers that the optical zone can provide different optical powers at different positions within the optical zone and thereby correct visions at different intermediate distances.

A "radial center", in reference to a rotationally asymmetrical progressive zone of an ophthalmic lens, refers to a first surface point at which the optical power of the lens turns into the near optical power when tracing from top to bottom along the vertical meridian or a line parallel to the vertical meridian and passing through the center of the central optical zone.

A "radiating semi-meridian", in reference to a rotationally asymmetrical progressive zone of an ophthalmic lens, refers to an imaginary line running radially from the radial center of the rotationally asymmetrical progressive zone to the peripheral boundary of the rotationally asymmetrical progressive zone on one of the anterior surface and posterior surface of a contact lens or on one of the two opposite surfaces of the central optical zone of an intraocular lens.

An "upper vertically radiating semi-meridian" refers to an imaginary line running upwardly and vertically from the radial center of a rotationally asymmetrical progressive zone to the upper boundary of the rotationally asymmetrical progressive zone on one of the anterior surface and posterior surface of a contact lens or on one of the two opposite surfaces of the central optical zone of an intraocular lens, when said lens is maintained at a predetermined orientation on or in an eye.

A "lower vertically radiating semi-meridian" refers to an imaginary line running downwardly and vertically from the radial center of a rotationally asymmetrical progressive zone to the lower boundary of the rotationally asymmetrical progressive zone on one of the anterior surface and posterior surface of a contact lens or on one of the two opposite surfaces of the central optical zone of an intraocular lens, when said lens is maintained at a predetermined orientation on or in an eye.

"The distance vision zone being located in the upper portion of the central optical zone" means that at least 60%, preferably, preferably at least 80%, more preferably at least 90%, of the distance vision zone is located in the half central optical zone above the horizontal meridian. It is understood that the distance vision zone can be larger than or smaller than or equal to the half central optical zone above the horizontal meridian.

"The rotationally-asymmetrical progressive zone being located in the lower portion of the central optical zone" means that at least 60%, preferably at least 80%, more preferably at least 90%, of the rotationally-asymmetrical progressive zone is located in the half central optical zone below the horizontal meridian. It is understood that the rotationally-asymmetrical progressive zone can be larger than or smaller than or equal to the half central optical zone below the horizontal meridian.

"The upper boundary of the rotationally-asymmetrical progressive zone" refers to one half peripheral boundary which is above a line parallel to the horizontal meridian and passing through the radial center.

"The lower boundary of the rotationally-asymmetrical progressive zone" refers to one half peripheral boundary which is below a line parallel to the horizontal meridian and passing through the radial center.

The central optical zone of a contact lens is generally surrounded by one or more peripheral zones that are adjacent to the optical zone and the boundary of a contact lens. A peripheral zone can be composed of one or more peripheral bands or regions which are patched together to form a continuous surface. The area of the peripheral zone typically can be equal to or larger than the area of the central optical zone, preferably is at least about 60% of the total area of the anterior surface of a contact lens.

Exemplary peripheral zones include without limitation bevel, lenticular, peripheral blending zone and the like.

A "bevel" refers to a non-optical surface zone located at the boundary of the posterior surface of a contact lens. Generally, the bevel is a significantly flatter curve and is usually blended with the base curve (optical posterior surface) of a contact lens and appears as an upward taper near the boundary. This keeps the steeper base curve radius from gripping the eye and allows the boundary to lift slightly. This boundary lift is important for the proper flow of tears across the cornea and makes the lens fit more comfortable.

"A lenticular" refers to a non-optical surface zone of the anterior surface of a contact lens between the optical zone and the boundary. The primary function of the lenticular is to control the thickness of the lens boundary.

A "peripheral blending zone" refers to a non-optical zone located between a lenticular zone and the central optical zone. The presence of a peripheral blending zone can allow to separately and independently design the central optical zone and the peripheral zone, so as to ensure a continuous transition from the central optical zone to the peripheral zone. With a peripheral blending zone between the central optical zone and the peripheral zone, a contact lens can be produced to have flexion points and/or sharp boundaries at the junction between two zones being eliminated and thereby provide improved wearer's comfort. In addition, the peripheral blend zone between the central optical zone and the peripheral zone can de-couple the optical features and the mechanical stabilization and translation features of the lens, thus preventing the introduction of prism into the optics. The peripheral blending zone has a surface that ensures that the peripheral zone, the blending zone and the central optical zone are tangent to each other. The blending zone of the invention can be any surface described by a mathematical function, preferably a spline-based mathematical function, or made of different tangent surface patches.

"Tangent surface patches" refer to combinations of surfaces with curvatures that are continuous in first derivative, preferably in second derivative, from each other.

The central optical zone of a contact lens can have any shape suitable for a contact lens design, for example, such as circular, oval, or the like. Preferably, the central optical zone is circular. More preferably, the central optical zone is a circular zone which is concentric with the geometric center of the anterior surface (or posterior surface), though the center of the central optical zone can be deviated from the geometric center of the anterior or posterior surface by up to 2 mm. Where the central optical zone is concentric with the geometric center of the anterior or posterior surface, the vertical and horizontal meridians each pass through the center of the central optical zone. Where the center of the central optical zone is deviated from the geometric center of the anterior or is posterior surface, a line parallel to the vertical or horizontal meridian passes through the center of the central optical zone.

A preferred embodiment of the distance zone is that it extends downwardly from the top boundary of the central optical zone. The lower boundary line of the distance zone with the rotationally-asymmetrical progressive zone is preferably slightly above (i.e., about 1 mm or less), more preferably at, even more preferably slightly below (i.e., about 1 mm or less) a horizontal line passing through the center of the central optical zone (the horizontal meridian or line parallel with the horizontal meridian), at least in its central portion (i.e., around the intersection point of the lower boundary line with the vertical meridian or with a line parallel to the vertical meridian and passing through the center of the central optical zone). The first optical zone can be defined by any mathematical function, for example, a spherical function, a conic function, a biconic function, Zernike polynomials, a spline-based mathematical function or combinations thereof.

The rotationally-asymmetrical progressive zone is located in the lower portion of the central optical zone. The radial center is located below the optical axis (i.e., the center) of the central optical zone and on the vertical meridian or a line parallel to the vertical meridian and passing through the center of the central optical zone. The distance between the radial center and the optical axis of the lens, the optical axis passing through the center of the central optical zone, is preferably about 2.0 mm or less. The rotationally-asymmetrical progressive zone can be defined by any mathematical function, for example, a spherical function, a conic function, a biconic function, Zernike polynomials, a spline-based mathematical function or combinations thereof.

The rotationally-asymmetrical progressive zone generally has a mirror symmetry with respect to a plane cutting through the upper and lower vertically radiating semi-meridians.

A preferred embodiment of the central optical zone is that the lateral separation between images from the distance vision zone and the rotationally-asymmetrical progressive zone is minimized or eliminated so as to minimize or eliminate ghost images. Ghost images are caused when the images from multiple optical zones, on an eye, have lateral separation. The images from both zones will have an axial separation, on an eye, typical of a bifocal lens. As embodied herein, a first line passing through the radial center of the progressive zone and the center of curvature at the radial center intersects a second line passing through the center of the central optical zone and the center of curvature at the apex of the posterior surface (i.e., optical axis), wherein the intersection point is within 2 mm or less of the center of curvature at the apex of the posterior surface. Such optical zone may properly align the lateral images near the optical axis of the lens and controls image jump (lateral separation) to the wearer.

In the preferred embodiment, the optimal alignment of the rotationally-asymmetrical progressive zone is controlled by rotating the rotationally-asymmetrical progressive zone around the radial center. To properly align the lateral images, the line passing through the radial center and the center of curvature at the radial center should pass through the center of curvature of the (posterior) base curve surface. However, in the preferred embodiment, the asymmetrical stabilization and/or translation features of the lens require that the line passing through the radial center and the center of curvature at the radial center intersects the central axis of the posterior (or base curve) surface slightly displaced of the center of curvature at the apex of the posterior surface.

Contact lenses of the invention can be either hard or soft lenses. Soft contact lenses of the invention are preferably made from a soft contact lens material, such as a silicon or fluorine-containing hydro-gel or HEMA. It will be understood that any lens material can be used in the production of an ophthalmic lens of the invention.

Figure 1B:
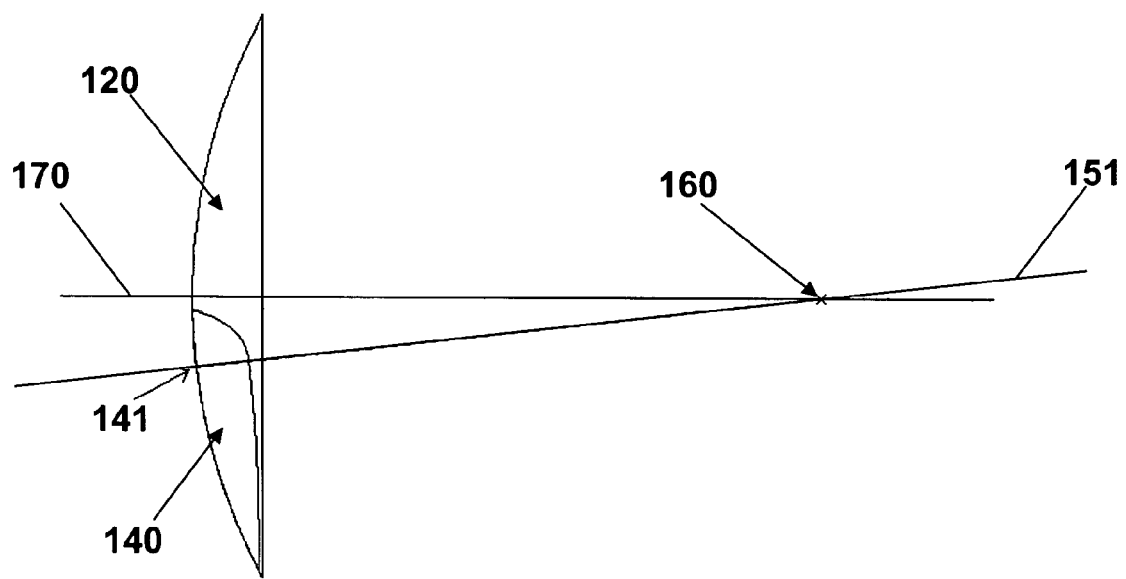

FIGS. 1A and 1B illustrate schematically the central optical zone 100 of the anterior surface of a contact lens according to a preferred embodiment of the invention. The anterior surface has a horizontal meridian 102, a vertical meridian 103 and the central optical zone 100 which is a circular zone concentric with the geometrical center of the anterior surface. Central optical zone 100 comprises a center 101, a distance vision zone 120, a rotationally-asymmetrical progressive zone 140, a top boundary 108, and a bottom boundary 109.

The rotationally-asymmetrical progressive zone 140 has a radial center 141, a upper boundary 143, a lower boundary 144, an upper vertically radiating semi-meridian 146, a lower vertically radiating semi-meridian 147, a left horizontally radiating semi-meridian 148, and a right horizontally radiating semi-meridian 149. The rotationally-asymmetrical progressive zone 140 is surrounded by the distance vision zone and has a surface that is tangent to the distance vision zone along the upper and lower boundaries (143, 144).

A line 151 passing through the radial center and the center of curvature at the radial center intersects with the optical axis 170 of the lens at the center 160 of curvature of the posterior (base curve) surface (FIG. 1B).

Optical power remains substantially constant along both the left and right horizontally radiating semi-meridians (148, 149), except in the region near the boundary. The surface near the upper and lower boundaries (143, 144) of the rotationally-asymmetrical progressive zone 140 is designed to have the rotationally-asymmetrical progressive zone 140 and the distance vision zone 120 tangent to each other along the boundary between them.

Figure 2A:
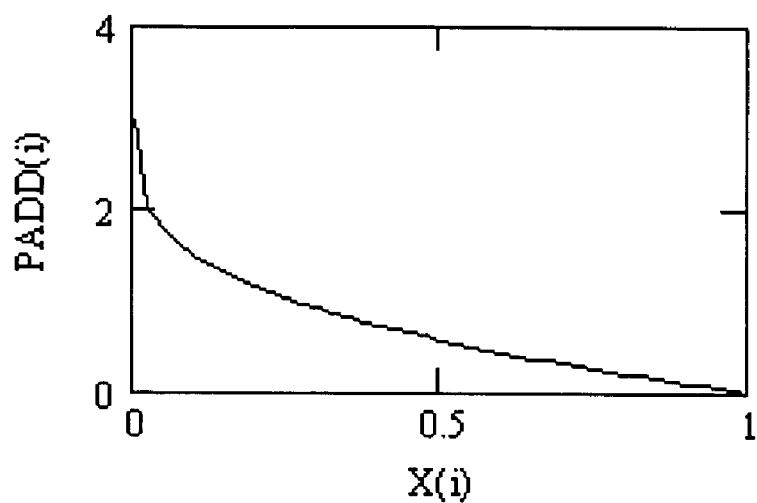
FIG. 2A shows schematically the optical power profile of a contact lens shown in FIGS. 1A and 1B along the upper vertically radiating semi-meridian (as function of radial distance from the radial center).

FIG. 2A shows schematically the optical power profile of the lens along the upper vertically radiating semi-meridian 146 (as function of radial distance from the radial center), according to a preferred embodiment. Optical power increases from the distance optical power at the upper boundary 143 (i.e., X(i)=1 mm) to the near optical power at the radial center (i.e., X(i)=0).

Figure 2B:
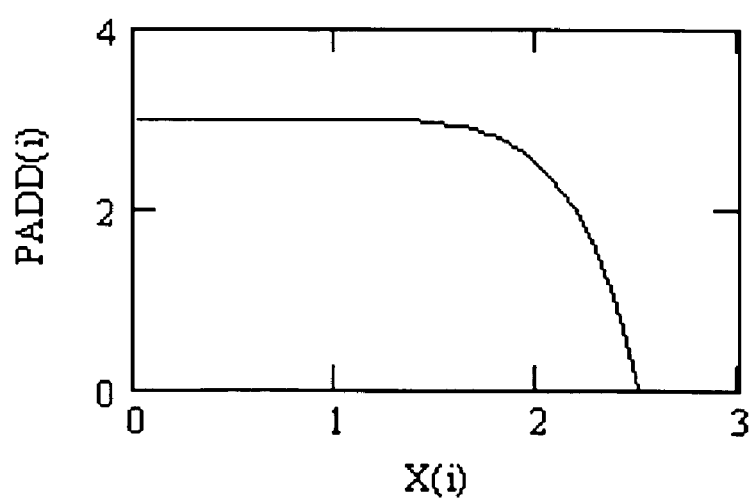
FIG. 2B shows schematically the optical power profile of a contact lens shown in FIGS. 1A and 1B along the lower vertically radiating semi-meridian (as function of radial distance from the radial center).

FIG. 2B shows schematically the optical power profile of the lens along the lower vertically radiating semi-meridian 147 (as function of radial distance from the radial center), according to a preferred embodiment. Optical power decreases from the near optical power at the radial center (i.e., X(i)=0) to the distance optical power at the lower boundary 144 (i.e., X(i)=2.5 mm). X(i) is a radial distance of point i from the radial center. A "radial distance" of a point from the radial center along a semi-meridian refers to the distance between the point and radial center projected on a plane (xy-plane) perpendicular to the central axis or optical axis.

It is understood that the optical power profile of the lens along the upper vertically radiating semi-meridian 146 can be defined by a plurality of (at least two) linear equations (1), $$\begin{cases} p(x) = b_1 + k_1 x & 0 \le x < x_1 \\ p(x) = b_2 + k_2 x & x_1 \le x < x_2 \\ \vdots & \\ p(x) = b_i + k_i x & x_{i-1} \le x < x_i \\ \vdots & \end{cases} \quad (1)$$

in which p(x) is an added power at a radial distance of x from the radial center; $b_i$ is a coefficient which is the intercept of a linear line; and $k_i$ is the rate of change of the added power as function of the distance from the radial center. $b_1$ can be considered as the added maximum power and can have a value from about 3 to 10, preferably a value of about 5. Each function defines an added power within a specific range, for example, between $x_{i-1}$ and $x_i$ within the progressive zone. In a preferred embodiment, the added power profile is defined by two or more linear functions.

Alternatively, the optical power profile of the lens along the upper vertically radiating semi-meridian 146 can be defined by equation (2) or equation (3), $$p(x) = \frac{A}{2} \cdot \cos\left(\frac{x}{X_o}\pi\right) + \frac{A}{2} \quad (2)$$

$$p(x) = A \cdot \left[1 - \left(\frac{x}{X_o}\right)^n\right] \quad (3)$$

in which p(x) is an added power at a radial distance of x from the radial center; A is the maximum added power; $X_o$ is the distance between the radial center and the optical axis of the lens; and n is any number which can be an integer or non-integer larger than 1 but smaller than or equal to 10. Preferably, n is larger than or equal to 3 but smaller than or equal to 5.

The invention, in another aspect, provides an intraocular lens capable of correcting presbyopia capable by providing distance, intermediate and near vision corrections. The intraocular lens can be phakic or aphakic. The intraocular lens comprises a central optical zone, the central optical zone having a first surface and an opposite second surface. At least one of the first and second surfaces includes a top boundary, a bottom boundary, a vertical meridian, a horizontal meridian, a distance vision zone and a rotationally-asymmetrical progressive zone adjacent to the distance vision zone. The distance vision zone is located in the upper portion of the optical zone and provides a distance power for distance vision correction. The rotationally-asymmetrical progressive zone is located in the lower portion of the optical zone and provides a variable intermediate vision correction and near vision correction. The rotationally-asymmetrical progressive zone has an upper boundary, a lower boundary, a radial center located in the vertical meridian and below the center of the optical zone. The rotationally-asymmetrical progressive zone further has a surface that provides a power profile that increases, along the vertical meridian, from the distance power at the upper boundary to a near power at the radial center and then remains substantially constant from the radial center to a point near bottom along the vertical meridian.

An intraocular of the invention can have one or more of the features described above for a contact lens of invention.

Where an ophthalmic lens of the invention is a contact lens, the contact lens preferably comprises one or more orientation/stabilization features. Any suitable orientation/ stabilization features can be used in the invention. Exemplary orientation/stabilization features include, without limitation, a prism ballast or the like that uses a varying thickness profile to control the lens orientation; a faceted surface in which parts of the lens geometry is removed to control the lens orientation; a ridge feature which orients the lens by interacting with the eyelid, double slab-off features which have a top slab-off zone and a bottom slab-off zone zones to maintain the lens orientation on the eye as well as a visual cue on the lenses so that a wearer can insert the lenses in the proper orientation; non-prism ballast features in the peripheral zone of the lens, disclosed in a co-pending U.S. patent application No. 60/401,736 filed on Aug. 6, 2002, entitled "Contact lenses" (herein incorporated by reference in its entirety); and the like.

Preferably, the orientation/stabilization features of a contact lens of invention comprises on the anterior surface of the lens a ramped ridge zone, which is described in a copending U.S. patent application No. 60/398/485 filed on Jul. 24, 2002, entitled "Translating Contact Lens Having A Ramped Ridge", herein incorporated by reference in its entirety. The ramped ridge zone is disposed below the optical zone and includes an upper boundary, a lower ramped boundary, a latitudinal ridge that extends outwardly from the anterior surface, and a ramp that extends dowardly from the lower ramped boundary and has a curvature or slope that provides a varying degree of interaction between the ramped ridge zone and the lower eyelid depending on where the lower eyelid strikes the ramped ridge zone. The lower eyelid of the eye is engaged with at least some portion of the ramped ridge zone at all times. Such ramped ridge zone can provide wearers comfort and also is capable of controlling contact lens position on an eye in primary gaze and/or translating amount across the eye when the eye changes from gazing at an object at a distance to gazing at an object at an intermediate distance or at a nearby object. Preferably, when transforming the design of an optimized optical model lens into a mechanical lens design, some common features of a family of contact lenses can be incorporated.

More preferably, the orientation/stabilization features of a contact lens of invention comprises non-prism ballast features in the peripheral zone of the lens, disclosed in a co-pending U.S. patent application No. 60/401,736 (incorporated herein by reference in its entirety. It was discovered that, when a contact lens has in the peripheral zone (non-optical zone surrounding the optical zone) a lens thickness profile characterized by having a thickness which increases progressively from the top of the lens downwardly along each of the vertical meridian and lines parallel to the vertical meridian until reaching a maximum value at a position between the optical zone and the boundary zone and then decreases to the boundary of the boundary zone, such contact lens can be maintained at a predetermined orientation on an eye. Like a conventional lens ballast, such orientation feature works by weighting the lens at the bottom, causing it to come to an equilibrium position on the eye. With such orientation feature, the optical zone of the anterior surface can be designed independently that can provide an optimal visual performance.

Where an ophthalmic lens of the invention is an intraocular lens (phakic or aphakic), the intraocular comprises haptics. Any known suitable haptics can be used in the present invention.

The central optical zone of an ophthalmic lens of the invention is designed according to a mathematical model, or alternative representation, that can provide optical power not only for distance vision correction but also for intermediate and near vision correction. It is well known to those skilled in the art that the optical power can be introduced in an ophthalmic lens by designing and optimizing the first surface and opposite second surface of the central optical zone or optical zone of an ophthalmic lens. For example, one can first design the first surface of an optical model lens in a form of mathematical description and then design and optimize the second surface of the model lens to impart to the model lens optical powers for distance, intermediate and near vision corrections, for example, by using ray tracing techniques. It is understood that either or both of the first and opposite second surface of an optical model lens can be optimized to produce variable optical powers for distance, intermediate and near vision corrections.

The ray tracing technique is well known in the art. Several commercially-available optical design software packages contain ray tracing programs. Exemplary optical design software packages include ZEMAX from ZEMAX Development Corporation.

An "optical model lens" refers to an ophthalmic lens that is designed in a computer system and generally does not contain other non-optical features that constitute an ophthalmic lens. Exemplary non-optical systems of a contact lens include, but are not limited to bevel, lenticular, orientation or stabilization features, and boundary that joins the anterior and posterior surfaces of a contact lens. Exemplary non-optical systems of an intraocular lens (phakic or aphakic) include without limitation haptics.

Any mathematical function can be used to describe the first surface and the opposite second surface of the central optical zone of an ophthalmic lens, as tong as they have sufficient dynamic range that allow the design of that lens to be optimized. Exemplary mathematical functions include conic, biconic and quadric functions, polynomials of any degree, Zernike polynomials; exponential functions, trigonometric functions, hyperbolic functions, rational functions, Fourier series, and wavelets. Preferably, a spline-based mathematical function or a combination of two or more mathematical functions are used to describe the first surface and second surface of an optical zone.

As an illustrative example, the central optical zone on the anterior surface of a contact lens shown in FIG. 1 can be designed as follows. A first optical surface is designed to provide a desired optical power for distance version correction. The central axis of the first optical surface coincides with the central axis of the posterior surface.

Then, the position of a radial center is determined. The radial center is placed in a plane cutting through a line being parallel or coinciding with the vertical meridian and passing through the center of the central optical zone. The radial center position is calculated and the radial center is positioned at a distance above at a position in space away from the first optical surface and, in the preferred embodiment, below the center of the central optical zone. The distance between the radial center and the first optical surface (i.e., height) and the distance between the radial center and the central axis passing through the center of the central optical zone (i.e., optical axis) are determined by the maximum amount of optical power added, the functional form defining power profile and local radial dimension. The axis of the radial center will pass through or near the center of curvature of the base curve apex.

After positioning the radial center, eight or more radiating semi-meridians, including at least an upper vertically radiating semi-meridian, a lower vertically radiating semi-meridian, a left horizontally radiating semi-meridian and a right horizontally radiating semi-meridian, are created that are radiating from the radial center to the first optical surface. All radiating semi-meridians are tangent to the first optical surface along the boundary line and have a curvature that provides a desired power profile and also ensures that a line passing through the radial center and the center of curvature at the radial center is normal to all semi-meridians. Two horizontally radiating semi-meridians (i.e., left and right semi-meridians parallel to the horizontal meridian) and all radiating semi-meridian below the two horizontally radiating semi-meridians will provides a constant optical power in major portion except in the region near the boundary line where each radiating semi-meridian is blended with the first optical surface. An upper vertically-radiating semi-meridian will provide a desired power profile that increase from the distance power at the upper boundary to the near power at the radial center according to a desired functional form. Other remaining radiating semi-meridians above the two horizontally radiating semi-meridians are preferably created to provide, along each lines parallel to the vertical meridian, a power profile substantially identical to the one provided by the upper vertically radiating semi-meridian. Each radiating semi-meridian can be obtained by a spline to connect points, each of which is calculated and positioned at a distance above at a position in space away from or on the first optical surface, to provide a desired optical power at that position. It is understood that the upper boundary of the rotationally-asymmetrical progressive zone can be an imaginary line formed based on a spline that connects last outbound points away from the radial center in all radiating semi-meridians.

Figure 3A:
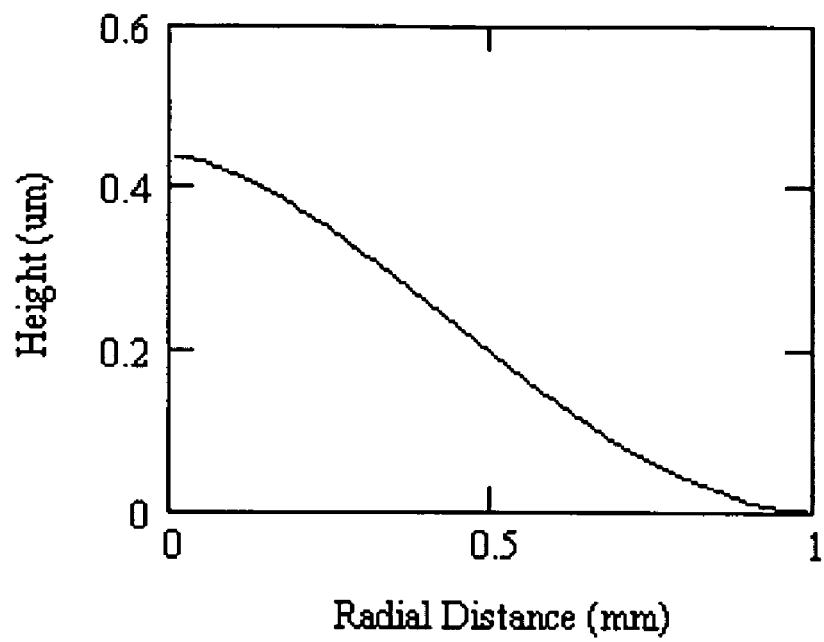
FIGS. 3A and 3B illustrate schematically the distance (i.e., height) between the first optical surface of a contact lens shown in FIGS. 1A and 1B and a point along the upper and lower vertically radiating semi-meridians on the second optical surface of the contact lens shown in FIGS. 1A and 1B.
Figure 3B:
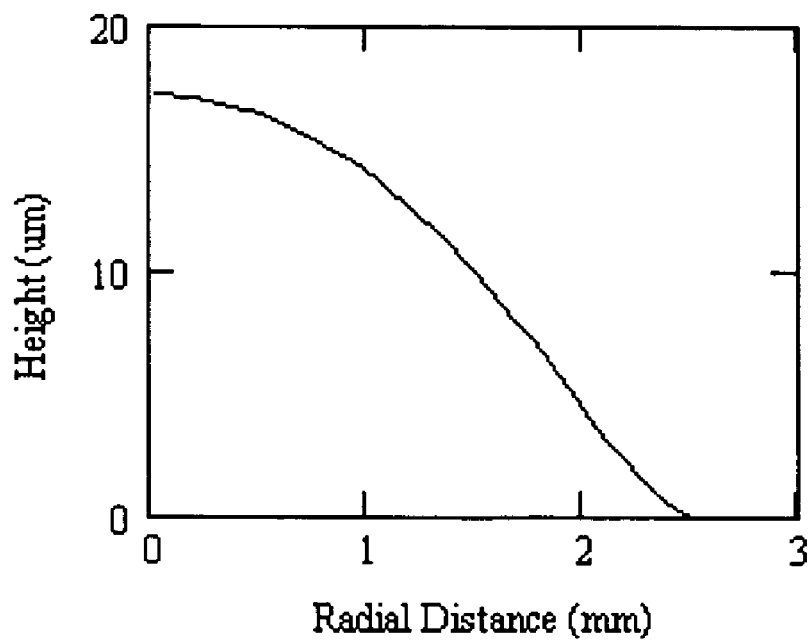

FIGS. 3A and 3B illustrate schematically the distance (i.e., height) between the first optical surface and a point along the upper and lower vertically radiating semi-meridians.

A second optical surface is created from the eight or more radiating semi-meridians according any known methods. The obtained central optical zone can be optimized to have optimized Point Spread Function or ghost image blur positions with minimal or no image jump.

It is understood that the boundary line of the distance vision zone with the rotationally-asymmetrical progressive zone can also be obtained by projecting a projecting curve on a plane (xy-plane) perpendicular to the central axis onto the first optical surface to form the boundary line of the distance vision zone with the rotationally-asymmetrical progressive zone. This boundary line defines the upper and lower boundaries of the rotationally-asymmetrical progressive zone.

An ophthalmic lens of the invention can be designed using any known, suitable optical design system. Exemplary optical computer aided design systems for designing an optical model lens includes, but are not limited to ZEMAX (ZEMAX Development Corporation). Preferably, the optical design will be performed using ZEMAX (ZEMAX Development Corporation). The design of the optical model lens can be transformed by, for example, a mechanical computer aided design (CAD) system, into a set of mechanical parameters for making a physical lens. Any know suitable mechanical CAD system can be used in the invention. The design of an optical model lens may be translated back and forth between the optical CAD and mechanical CAD systems using a translation format which allows a receiving system, either optical CAD or mechanical CAD, to construct NURBs (non-uniform rational B-splines), Bézier surfaces of an intended design or ASCII parameters that control a parametric design. Exemplary translation formats include, but are not limited to, VDA (verband der automobilindustrie) and IGES (Initial Graphics Exchange Specification). By using such translation formats, overall surface of lenses can be in a continuous form that facilitates the production of lenses having radial asymmetrical shapes. Bézier and NURBs surface are particular advantageous for a lens having a plurality of zones including optical zone and non-optical zones because multiple zones can be blended, analyzed and optimized. More preferably, the mechanical CAD system is capable of representing precisely and mathematically high order surfaces. An example of such mechanical CAD system is Pro/Engineer from Parametric Technology.

When transforming the design of an optical model lens into a set of mechanical parameters, common feature parameters of a family of ophthalmic lenses can be incorporated in the lens designing process. Examples of such parameters include shrinkage, non-optical boundary zone and its curvature, center thickness, range of optical power, and the like.

An ophthalmic lens of the invention may be produced by any convenient manufacturing means, including, for example, a computer-controllable manufacturing device, molding or the like. A "computer controllable manufacturing device" refers to a device that can be controlled by a computer system and that is capable of producing directly an ophthalmic lens or optical tools for producing an ophthalmic lens. Any known, suitable computer controllable manufacturing device can be used in the invention. Exemplary computer controllable manufacturing devices includes, but are not limited to, lathes, grinding and milling machines, molding equipment, and lasers. Preferably, a computer controllable manufacturing device is a two-axis lathe with a 45° piezo cutter or a lathe apparatus disclosed by Durazo and Morgan in U.S. Pat. No. 6,122,999 (herein incorporated by reference in its entirety), or is a numerically controlled lathe, for example, such as Optoform® ultra-precision lathes (models 30, 40, 50 and 80) having Variform® or Varimax piezo-ceramic fast tool servo attachment from Precitech, Inc.

Preferably, contact lenses are molded from contact lens molds including molding surfaces that replicate the contact lens surfaces when a lens is cast in the molds. For example, an optical cutting tool with a numerically controlled lathe may be used to form a metallic optical tool incorporating the features of the anterior surface of a contact lens of the invention. The tool is then used to make anterior surface molds that are then used, in conjunction with posterior surface molds, to form the lens of the invention using a suitable liquid lens-forming material placed between the molds followed by compression and curing of the lens-forming material.

Preferably, an ophthalmic lens of the invention or the optical tool to be used for making the same is fabricated by using a numerically controlled lathe, for example, such as Optoform® ultra-precision lathes (models 30, 40, 50 and 80)

having Variform® or Varimax piezo-ceramic fast tool servo attachment from Precitech, Inc, according to a method described in a co-pending U.S. Patent Application of CibaVision, entitled Method for Manufacturing a contact lens, (U.S. Ser. No. 60/398,495, filed on Jul. 24, 2002), herein incorporated by reference in its entirety.

As an illustrative example, production of a translating contact lens having a ramped ridge zone having a latitudinal ridge is created via the following process. First, a user defines a set of parameters, such as a surface tolerance, a concentricity tolerance, orientation of the lens design, the number of semi-diameter spokes to be generated for each of the anterior and posterior surfaces, creating zero point at 0,0, orientation of Z-axis, and type of lens surface (concave or convex surface) to be converted into a geometry. A "surface tolerance" refers to the allowed position-deviation of a projected point from an ideal position on a surface of a lens design. The deviation can be in the direction either parallel or perpendicular to the central axis of a lens design. A "concentricity tolerance" refers to the allowed deviation of a point from a given arc. A "semi-diameter spoke" refers to a curve radiating outwardly from the central axis and is perpendicular to the central axis and projected onto the surface. "Evenly-spaced semi-diameter spokes" means that all semi-diameter spokes radiate outwardly from the central axis and separate from each other by one equal angle. A "point spacing" refers to a distance between two points along the semi-diameter spoke.

Second, a user determines the point density to be projected onto the surface of the lens design (for example, the anterior surface) along each of the number of evenly-spaced semi-diameter spokes in a direction parallel to the central axis. A semi-diameter spoke at an azimuthal angle corresponds to the feature that deviates most from the base conic surface, and is selected as the semi-diameter probing spoke. Evenly-spaced points are projected along the semi-diameter probing spoke, in which each pairs of points are separating by a point spacing of typically 10 microns. Then all of the projected points are divided into a series of groups, with each group composed of three consecutive points, a first point, a middle point, and a third point. Each of the points can belong to either one group or two groups. One group is analyzed at a time from the central axis to the boundary, or from the boundary to the central axis, from the curvature of the surface at the middle point of the group by comparing a distance between the middle point and a line linking the first point and the third point of the corresponding group with the predetermined surface tolerance. If the distance between the middle point and the line linking the first and third points of the group is larger than the predetermined surface tolerance, the curvature of the surface at that point is sharp and an additional point is projected between the first and the middle points in that group. The point spacing between the first and additional points is equal to point spacing between the additional and middle points. After adding an additional point, all of the points included the newly added point is regrouped again and the curvature of the surface at the middle point of each of the series of groups is analyzed. Such iterative procedure is repeated until the distance between the middle point of each of the series of groups and the line linking the first and the third points of corresponding group along the probing spoke is equal to or less than the predetermined surface tolerance. In this manner, the number of the points to be projected onto the surface of the lens design along each of the desired number of evenly-spaced semi-diameter spokes and point spacing for a series of pairs of neighboring points are determined.

The above-determined number of points is then projected onto the anterior surface of the lens design along each of 24, 96 or 384 semi-diameter spokes, in the preferred embodiment. Other numbers of spokes are possible. For each of the semi-diameter spokes, a semi-meridian that is continuous in first derivative is generated. The semi-meridian includes a series of arcs and, optionally, straight lines wherein each arc is defined by fitting at least three consecutive points into a spherical mathematical function within a desired concentricity tolerance. Each of the straight lines is obtained by connecting at least three consecutive points. Preferably, the arc-fitting routine is started from the central axis to the boundary. Similarly, conversion of the posterior surface of the lens design into geometry can be carried out according to the above-described procedure.

After converting the lens design to geometry of a contact lens to be produced in a manufacturing system, a mini-file, or equivalent format, containing both the information for the header and the information about the geometry of the lens is generated. This mini-file also contains a zero semi-meridian that is based on the average height of each of the other meridians at each of radial locations and that gives the Variform or Varimax a zero position on which it can base its oscillation calculations. In this mini-file, all semi-meridians have the same number of zones. This is accomplished by copying the last zone of a semi-meridian for a number of times to equalize the numbers of zones for all meridians. After the mini-file is completed, it is loaded into an Optoform® ultra-precision lathe (models 30, 40, 50 or 80) having Variform® piezo-ceramic fast tool servo attachment and run to produce a translating contact lens.

An ophthalmic lens of the invention can be characterized by any known suitable optical metrology system. The vertically oriented coma-like and other wavefront aberrations of the lens can be determined by any suitable methods known to one skilled in the art, including without limitation, Shack-Hartmann techniques, Tscherning techniques, retinal ray tracing techniques, and spatially-resolved refractometer techniques.

The present invention also provides a method of manufacturing an ophthalmic lens of the invention.

The invention, in still another aspect, provides a method for producing a contact lens capable of correcting presbyopia by providing distance, intermediate and near vision corrections. The method comprises the steps of designing the anterior surface and the posterior surface of the contact lens, wherein one of the anterior and posterior surface, preferably the anterior surface, includes a vertical meridian, a horizontal meridian, a central optical zone having a top boundary, a bottom boundary, a distance vision zone and a rotationally-asymmetrical progressive zone adjacent to the distance vision zone. The distance vision zone is located in the upper portion of the central optical zone and provides a distance power for distance vision correction. The rotationally-asymmetrical progressive zone is located in the lower portion of the central optical zone and provides a variable intermediate vision correction and near vision correction. The rotationally-asymmetrical progressive zone has an upper boundary, a lower boundary, a radial center, an upper vertically radiating semi-meridian and a lower vertically radiating semi-meridian. The rotationally-asymmetrical progressive zone further has a surface that provides a power profile that increases, along the upper vertically radiating semi-meridian, from the distance power at the upper boundary to a near power at the radial center and remains substantially constant from the radial center to a point near the lower boundary along the lower vertically radiating semi-meridian.

The invention, in a further aspect, provides a method for producing an intraocular contact lens capable of correcting presbyopia by providing distance, intermediate and near vision corrections. The method comprises the steps of designing the intraocular lens which comprises a central optical zone, the central optical zone having a first surface and an opposite second surface. At least one of the first and second surfaces includes a top boundary, a bottom boundary, a vertical meridian, a horizontal meridian, a distance vision zone and a rotationally-asymmetrical progressive zone adjacent to the distance vision zone. The distance vision zone is located in the upper portion of the central optical zone and provides a distance power for distance vision correction. The rotationally-asymmetrical progressive zone is located in the lower portion of the central optical zone and provides a variable intermediate vision correction and near vision correction. The rotationally-asymmetrical progressive zone has an upper boundary, a lower boundary, a radial center located in the vertical meridian and below the center of the optical zone. The rotationally-asymmetrical progressive zone further has a surface that provides a power profile that increases, along the vertical meridian, from the distance power at the upper boundary to a near power at the radial center, and then remains substantially constant from the radial center to a point near the lower boundary along the vertical meridian.

The manufacturing method of the invention preferably further comprises a step of producing an ophthalmic lens by a manufacturing means as described above.

The present invention, in a still further aspect, provides a method for correcting presbyopia. The method of the invention comprises the step of reshaping the central vision area of the cornea of an eye to produce an optical zone, which includes a vertical meridian, a horizontal meridian, a top boundary, a bottom boundary, a distance vision zone and a rotationally-asymmetrical progressive zone adjacent to the distance vision zone. The distance vision zone is located in the upper portion of the central vision area and provides a distance power for distance vision correction. The rotationally-asymmetrical progressive zone is located in the lower portion of the central vision area and provides a variable intermediate vision correction and near vision correction. The rotationally-asymmetrical progressive zone has an upper boundary, a lower boundary, a radial center located in the vertical meridian of the central vision area and below the center of the central vision area. The rotationally-asymmetrical progressive zone further has a surface that provides a power profile that increases, along the vertical meridian, from the distance power at the upper boundary to a near power at the radial center, and then remains substantially constant from the radial center to a point near the lower boundary along the vertical meridian.

The cornea may be reshaped on the anterior or an underlying surface by ablation or collagen shrinkage, wherein the ablation is performed by applying an excimer laser, surgical laser, Water cutting, fluid cutting, liquid cutting or gas cutting technique. The laser surgery system includes a laser beam generator and a laser beam controller to regulate the beam striking the cornea to remove a selected volume of corneal tissue from a region in an optical zone of the cornea with the ablative radiation, thereby forming a reprofiled region which has a distance vision zone located in the upper portion of the central vision area on the cornea (i.e., optical zone of the cornea), a rotationally-asymmetrical progressive zone located in the lower portion of the central vision area on the cornea (i.e., optical zone), and a third vision area surrounding the second vision area.

Any known suitable ablation methods can be used. One ablating method according to the invention is to control energy distribution of a laser beam on an optical surface of the cornea. Another ablating method, according to the invention, is to control a flying spot laser pattern on the optical surface of the cornea. Yet another ablating method, according to the invention, is to control angle of ablation on the optical surface of the cornea. Yet another ablating method, according to the invention, is to ablate the cornea according to a mathematical model.

A "vertical meridian", in reference to a central vision area (i.e., optical zone), refers to an imaginary line running vertically from the top, through the center, to the bottom on the optical zone. A "horizontal meridian", in reference to a central vision area (i.e., optical zone), refers to an imaginary line running horizontally from the left side, through the center, to the right side on the optical zone. The horizontal and vertical meridians are perpendicular to each other.

A "top boundary", in reference to the optical zone produced on or in a cornea according to a method of the invention, refers to a portion of the peripheral boundary of the optical zone, which is above the horizontal meridian and around the intersection of the vertical meridian with the peripheral boundary.

A "bottom boundary", in reference to the optical zone produced on or in a cornea according to a method of the invention, refers to a portion of the peripheral boundary of the central optical zone, which is below the horizontal meridian and around the intersection of the vertical meridian with the peripheral boundary.

A "radial center", in reference to a rotationally asymmetrical progressive zone of an optical zone produced on or in a cornea according to a method of the invention, refers to a first surface point at which the optical power turns into the near optical power when tracing from top to bottom along the vertical meridian.

An "upper vertically radiating semi-meridian", in reference to a rotationally asymmetrical progressive zone of an optical zone produced on or in a cornea according to a method of the invention, refers to a segment of the vertical meridian between the radial center to the upper boundary of the rotationally asymmetrical progressive zone.

A "lower vertically radiating semi-meridian", in reference to a rotationally asymmetrical progressive zone of an optical zone produced on or in a cornea according to a method of the invention, refers to a segment of the vertical meridian between the radial center to the lower boundary of the rotationally asymmetrical progressive zone.

"The distance vision zone being located in the upper portion of the optical zone", in reference to the optical zone produced on or in a cornea according to a method of the invention, means that at least 70%, preferably, preferably at least 80%, more preferably at least 90%, of the distance vision zone is located in the half central optical zone above the horizontal meridian. The functional form of the ADD will determine the optimal portion of the zones to be subtended by the pupil for distance, intermediate and near vision.

"The rotationally-asymmetrical progressive zone being located in the lower portion of the central optical zone", in reference to the optical zone produced on or in a cornea according to a method of the invention, means that at least 70%, preferably, preferably at least 80%, more preferably at least 90%, of the rotationally-asymmetrical progressive zone is located in the half central optical zone below the horizontal meridian.

"The upper boundary of the rotationally-asymmetrical progressive zone", in reference to the optical zone produced on or in a cornea according to a method of the invention, refers to one half peripheral boundary which is above a line parallel to the horizontal meridian and passing through the radial center.

"The lower boundary of the rotationally-asymmetrical progressive zone", in reference to the optical zone produced on or in a cornea according to a method of the invention, refers to one half peripheral boundary which is below a line parallel to the horizontal meridian and passing through the radial center.

The above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. A method for correcting presbyopia, comprising the steps of:
reshaping the central vision area of the cornea of an eye to produce an optical zone, which includes a vertical meridian, a horizontal meridian, a top boundary, a bottom boundary, a distance vision zone and a rotationally-asymmetrical progressive zone adjacent to the distance vision zone,
wherein the distance vision zone is located in the upper portion of the central vision area and provides a distance power for distance vision correction;
wherein the rotationally-asymmetrical progressive zone is located in the lower portion of the central vision area and includes a variable intermediate vision correction zone and a near vision correction zone; wherein the rotationally-asymmetrical progressive zone has an upper boundary, a lower boundary, a radial center located in the vertical meridian of the central vision area and below the center of the central vision area; and
wherein the rotationally-asymmetrical progressive zone further has a surface that provides a power profile that increases, along the vertical meridian in the variable intermediate vision correction zone, from the distance power at the upper boundary to a near power at the radial center, and then remains substantially constant in the near vision correction zone from the radial center to a point near the lower boundary along the vertical meridian.

2. The method of claim 1, wherein the step of reshaping occurs by cornea ablation or collagen shrinkage.

3. The method of claim 2, wherein the step of reshaping occurs by cornea ablation.

4. The method of claim 3, wherein the ablation is performed by applying an excimer laser, surgical laser, water cutting, fluid cutting, liquid cutting or gas cutting technique.

5. The method of claim 3, wherein the ablation is performed by controlling energy distribution of a laser beam on an optical surface of the cornea.

6. The method of claim 3, wherein the ablation is performed by controlling a flying spot laser pattern on an optical surface of the cornea.

7. The method of claim 3, wherein the ablation is by controlling angle of ablation on an optical surface of the cornea.

8. The method of claim 1, wherein the distance zone extends downwardly from the top boundary of the central vision area; wherein the lower boundary line of the distance zone with the rotationally-asymmetrical progressive zone is at or slightly below a horizontal line passing through the center of the central vision area and parallel with the horizontal meridian, at least in its central portion.

9. The method of claim 8, wherein the apex of the distance vision zone coincides with the center of the central vision area.

10. The method of claim 1, wherein the radial center is located below the center of the central vision area and on the vertical meridian, and wherein the radial distance between the radial center and the center of the central vision area is about 2.0 mm or less.

11. The method of claim 1, wherein the rotationally-asymmetrical progressive zone is tangent to the distance vision zone at any point along the upper and lower boundaries of the rotationally-asymmetrical progressive zone.

12. The method of claim 1, wherein the rotationally-asymmetrical progressive zone has a surface that provides a power addition profile, along the vertical meridian, which is defined by two or more linear functions of equation (1) or by equation (2) or (3)

$$\begin{cases} p(x) = b_1 + k_1 x & 0 \leq x < x_1 \\ p(x) = b_2 + k_2 x & x_1 \leq x < x_2 \\ \vdots \\ p(x) = b_i + k_i x & x_{i-1} \leq x < x_i \\ \vdots \end{cases} \quad (1)$$

$$p(x) = \frac{A}{2} \cdot \cos\left(\frac{x}{X_o}\pi\right) + \frac{A}{2} \quad (2)$$

$$p(x) = A \cdot \left[1 - \left(\frac{x}{X_o}\right)^n\right] \quad (3)$$

in which p(x) is an added power at a radial distance of x from the radial center; $b_i$ is a coefficient which is the intercept of a linear line; $k_i$ is the rate of change of the added power as function of the distance from the radial center; A is the maximum added power; $X_o$ is a radial distance between the radial center and the optical axis; and n is any number which can be an integer or non-integer larger than 1 but smaller than or equal to 10.

* * * * *